United States Patent [19]
Coleman

[11] Patent Number: 4,617,923
[45] Date of Patent: Oct. 21, 1986

[54] SLING

[76] Inventor: Michael Coleman, 6666 Security Blvd., Baltimore, Md. 21207

[21] Appl. No.: 694,349

[22] Filed: Jan. 24, 1985

[51] Int. Cl.[4] ............................................. A61F 5/40
[52] U.S. Cl. .................................................... 128/94
[58] Field of Search ..................... 128/94, 87 R, 89 R, 128/77; 272/68

[56]  References Cited
U.S. PATENT DOCUMENTS

| | | | |
|---|---|---|---|
| 896,674 | 8/1908 | Walker | 128/89 R |
| 1,607,022 | 11/1926 | Swinburne | 272/68 |
| 3,547,112 | 12/1970 | Courtney | 272/68 |
| 4,510,928 | 4/1985 | Ackley | 128/94 |

FOREIGN PATENT DOCUMENTS

| | | | |
|---|---|---|---|
| 2549169 | 5/1976 | Fed. Rep. of Germany | 128/87 R |
| 892491 | 3/1962 | United Kingdom | 128/89 R |

OTHER PUBLICATIONS

"Coach and Athlete", p. 59, 1/2/1982.

Primary Examiner—Robert Peshock
Assistant Examiner—Cary E. Stone
Attorney, Agent, or Firm—Walter G. Finch

[57] ABSTRACT

The invention concerns an arm sling for preventing contracture of hand muscles, wherein the pocket portion is provided with a hole that interlocks with a grasping tube. A patient's fingers exit the sling via the hole and wrap about the grasping tube, the fingers being secured there about by a velcro fastened wrap.

5 Claims, 4 Drawing Figures

SLING

BACKGROUND OF THE INVENTION

The invention concerns an arm sling for use by stroke victims.

Thousands of stroke victims each year suffer a loss of limb use, the pathways from the brain to the limb having been destroyed or damaged as a result of the stroke. The muscles of the useless limb begin to atrophy and/or contract pulling the hand, for instance, into unnatural poses. In the case of an arm which is rendered useless by a stroke, the arm is typically carried in a sling. Such a sling may comprise nothing more than a triangular cloth which is slung over the shoulder of the patient, where two corners of the triangular cloth are tied together to form the sling. Commercial slings are also available which include large cloth pockets in which the arm rests and is provided with adjustable belts that pass behind the patient's back and over the opposite shoulder for support.

SUMMARY AND OBJECTS OF THE INVENTION

The invention concerns a sling for use particularly by stroke victims. The sling includes a pocket portion which supports the stroke victim's arm by means of straps that pass over the shoulder of the opposite arm. A hole is provided in the hand end of the sling. A generally cylindrical structure or grasping tube is also provided at the hand end of the sling such that the hole and grasping tube interlock. The hole forms a material ring of fabric in the pocket portion which interlocks with the grasping tube. A patient wears the sling such that the patient's hand exits the sling at the hole and wraps about the cylindrical grasping tube. As such, the muscles of a wearer's hand will not suffer contracture, the muscles being maintained rather than allowed to degenerate. A fastener is provided at the end of the sling which wraps over the wearer's fingers and fastens to the outside of the sling. The fastener may comprise a "velcro" fastener and is utilized to stabilize the hand in its position about the cylindrical member.

It is an object of the present invention to provide a sling with a means for preventing contracture of a patient's hand muscles.

Another object of the present invention is to provide a cylindrical grasping tube attached to a sling, about which a patient's fingers are wrapped, providing maintenance of the finger and hand muscles.

DETAILED DESCRIPTION OF THE INVENTION

Figure 1:
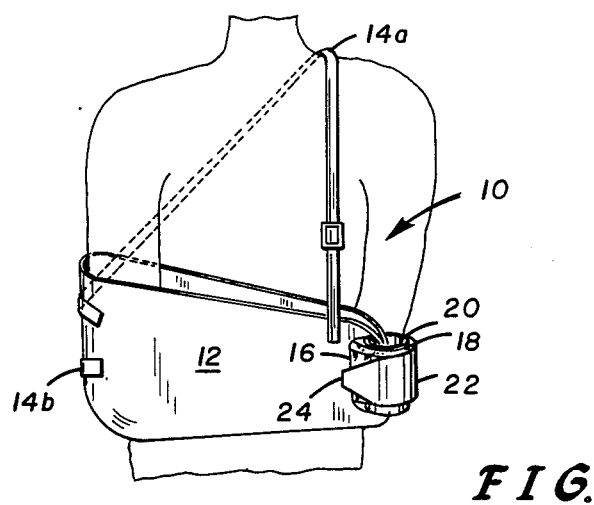
FIG. 1 shows a sling according to the present invention as worn by the patient.

FIG. 1 shows a patient wearing a shoulder sling in accordance with the principles of the present invention, generally shown at 10. The sling includes a pocket portion 12 which is supported via straps 14a by the shoulder of the patient. A second strap 14b passes around the patient's back to prevent swinging of the patient's arm. A hole 16 is provided in the distal end of the pocket portion through which the fingers 18 of the patient pass.

A cylindrical grasping tube 20 is interlocked with pocket portion 12 at hole 16 such that fabric of the pocket portion 12 passes through the hollow of the grasping tube. The fingers 18 of the patient are positioned to wrap about the grasping tube 20, counterclockwise as viewed in FIG. 1. The patient's thumb, however, wraps about the grasping tube in a clockwise manner. As such, the patient's hand maintains a C-shape about the grasping tube 20. The grasping tube 20 is dimensioned to generally approximate the lines of a hand which is curved in this manner. A patient who has lost motor control of his or her fingers will not suffer contracture of the finger and hand muscles, the grasping tube maintaining the muscles in a substantially normal pose. A wrap 22 is provided, which is sewn at one end (not shown) and includes a velcro fastener 24 at a second end. The wrap 22 is pulled against the patient's fingers 18 and is fastened via the velcro fastener 24 to the pocket portion 12. As such, fingers 18 are secured about the grasping tube 20 in a manner which prevents the fingers 18 from being pulled into an open position by muscle contracture in the opposite direction. Accordingly, the grasping tube 20 provides maintenance of a patient's hand and finger muscles while recovering from a stroke, for instance. If desired, two velcro fastener straps can be used, with one holding the fingers 18 and the other holding the thumb. The sling can be made either way, if it is so required.

Figure 2:
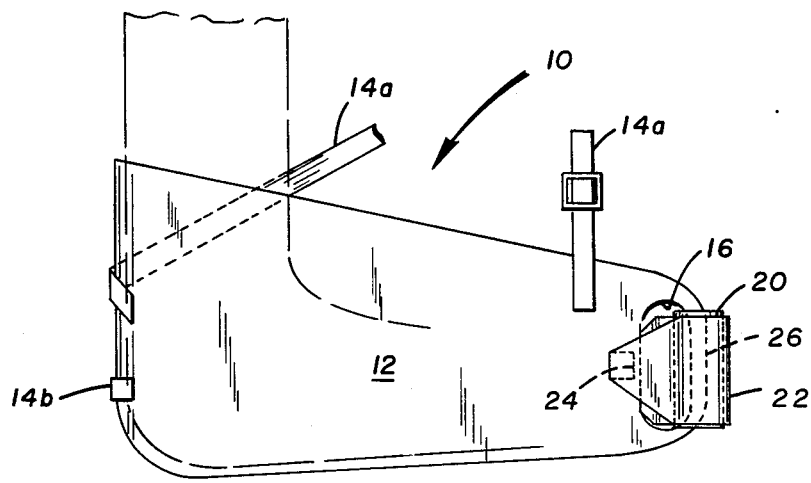
FIG. 2 shows a side view of the sling.

FIG. 2 shows the sling in accordance with the present invention in greater detail. Here, it is evident that hole 16 end grasping to 20 interlock, some fabric 26 of the pocket portion 12 passing through the hollow of the grasping tube 20.

Figure 3:
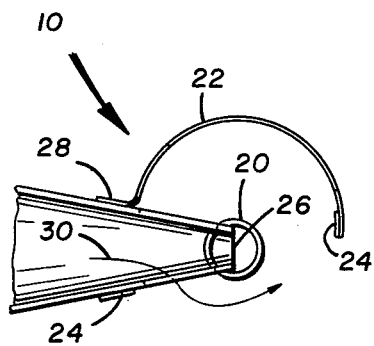
FIG. 3 shows a top view of the hand-end of the sling.

FIG. 3 shows a top view of the distal end of the pocket portion 12. The wrap 22 is shown as being sewn at 28. The fabric 26 of the pocket portion 12 is shown within the hollow of the grasping tube 20. A patient's fingers follow the path 30 through hole 16 and about the grasping tube 20. The wrap 22 is placed over the fingers and connects to the velcro fastener 24.

Figure 4:
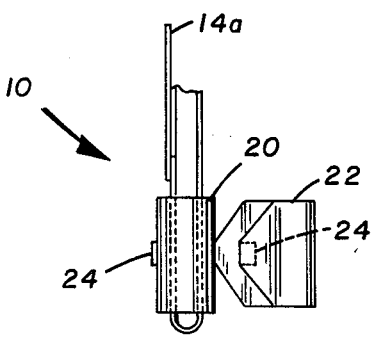
FIG. 4 shows an end view of the sling.

FIG. 4 shows an end view of the distal end of the sling 10. The relationship of the wrap 22 to the pocket portion 12 is evident. The wrap 22 is sewn to the right side of the pocket portion 12 (as viewed in FIG. 4) and fastens on the left side via velcro fastener 24.

What is claimed is:
1. An arm sling having a pocket portion in which a patient's arm is supported, a supporting means; and
a grasping means which is grasped by a patient's hand to maintain the muscles of the hand and prevent contracture thereof, grasping means comprising a grasping tube about which said patient's hand fits, said sling having a hole at a sling distal end through which fingers of the patient's hand pass, said sling hole and said grasping tube being arranged to interlock, said grasping tube being hollow so that a portion of said sling adjacent to said sling hole, is within said hollow of said grasping tube, said sling including a securing means which holds said patient's fingers about said grasping tube.
2. An arm sling as recited in claim 1, wherein said securing means comprises a wrap which extends from the distal end of said sling.
3. An arm sling as recited in claim 2, and additionally a fastening means attached to said wrap which fastens said wrap about said patient's fingers and to said sling pocket portion.

4. An arm sling as recited in claim 3, wherein said fastening means comprises a VELCRO fastener.

5. An arm sling having a pocket portion in which a patient's arm is supported, a supporting means,
- a grasping means which is grasped by a patient's hand to maintain the muscles of the hand and prevent contracture thereof,
- a securing means which holds the patient's hand about said grasping means, said grasping means comprising a grasping tube about which said patient's hand is shaped, with said securing means comprising a wrap which extends from the sling distal end, a fastening means attached to said wrap which fastens said wrap about said patient's fingers and to said sling pocket portion, said sling having a hole at a distal end of said sling through which fingers of said patient's hand pass, with said sling hole and grasping tube being arranged to interlock, said grasping tube being hollow, wherein a portion of the sling adjacent to the sling hole, is within said hollow of said grasping tube, and wherein said fastening means comprises a VELCRO fastener.

* * * * *